(12) United States Patent
Trieu

(10) Patent No.: US 7,445,634 B2
(45) Date of Patent: Nov. 4, 2008

(54) ANNULUS REPAIR SYSTEMS AND METHODS

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 482 days.

(21) Appl. No.: 10/399,308

(22) PCT Filed: Oct. 26, 2001

(86) PCT No.: PCT/US01/50177

§ 371 (c)(1),
(2), (4) Date: Apr. 15, 2003

(87) PCT Pub. No.: WO02/058599

PCT Pub. Date: Aug. 1, 2002

(65) Prior Publication Data

US 2004/0039392 A1    Feb. 26, 2004

Related U.S. Application Data

(60) Provisional application No. 60/243,941, filed on Oct. 27, 2000.

(51) Int. Cl.
*A61F 2/44* (2006.01)
(52) U.S. Cl. .......... 623/17.11; 623/17.16; 606/232; 606/246
(58) Field of Classification Search ............ 606/61, 606/232, 246; 623/17.11, 17.12, 17.13, 17.14, 623/17.15, 17.16
See application file for complete search history.

(56) References Cited

U.S. PATENT DOCUMENTS

| 4,329,743 A | 5/1982 | Alexander et al. |
| 4,411,027 A | 10/1983 | Alexander et al. |
| 4,790,303 A * | 12/1988 | Steffee .................. 606/61 |
| 4,919,667 A | 4/1990 | Richmond |
| 4,955,908 A | 9/1990 | Frey et al. |
| 5,067,964 A | 11/1991 | Richmond et al. |
| 5,108,438 A | 4/1992 | Stone |
| 5,549,679 A | 8/1996 | Kuslich |
| 5,571,189 A | 11/1996 | Kuslich |
| 5,609,634 A | 3/1997 | Voydeville |
| 5,681,353 A | 10/1997 | Li et al. |
| 5,725,582 A | 3/1998 | Bevan et al. |
| 5,735,903 A | 4/1998 | Li et al. |
| 5,888,220 A | 3/1999 | Felt et al. |
| 5,980,504 A | 11/1999 | Sharkey et al. |
| 6,007,570 A | 12/1999 | Sharkey et al. |
| 6,066,175 A | 5/2000 | Henderson et al. |
| 6,073,051 A | 6/2000 | Sharkey et al. |

(Continued)

FOREIGN PATENT DOCUMENTS

WO    WO 9961084 A1 * 12/1999

*Primary Examiner*—David H. Willse
*Assistant Examiner*—Javier G Blanco
(74) *Attorney, Agent, or Firm*—William R. Richter

(57) ABSTRACT

Systems and methods for repairing annulus defects include scaffold (30), attachment members (40), and anchors (20). The scaffold (30) acts as a plug to substantially fill the annulus defect. The anchors (20) are secured to tissue adjacent the annulus defect. The attachment member (40) secures the scaffold (30) to the anchors (2). Thus, the systems and methods for repairing annulus defects retain the scaffold within the annulus defect.

20 Claims, 7 Drawing Sheets

U.S. PATENT DOCUMENTS

| | | |
|---|---|---|
| 6,093,205 A | 7/2000 | McLeod et al. |
| 6,095,149 A | 8/2000 | Sharkey et al. |
| 6,224,630 B1 | 5/2001 | Bao et al. |
| 6,245,107 B1 | 6/2001 | Ferree |
| 6,264,656 B1 | 7/2001 | Michelson |
| 6,306,170 B2 * | 10/2001 | Ray .................. 623/17.11 |
| 6,371,990 B1 | 4/2002 | Ferree |
| 6,425,919 B1 | 7/2002 | Lambrecht |
| 6,592,625 B2 | 7/2003 | Cauthen |
| 6,827,743 B2 * | 12/2004 | Eisermann et al. ...... 623/23.54 |

* cited by examiner

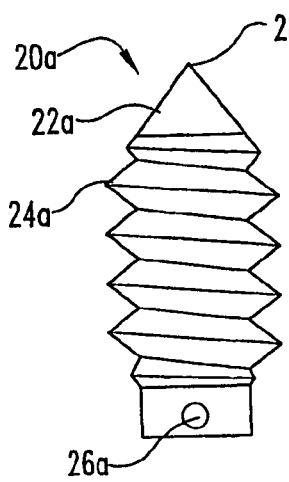
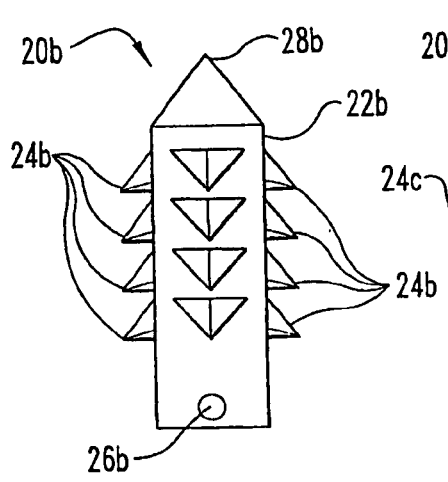
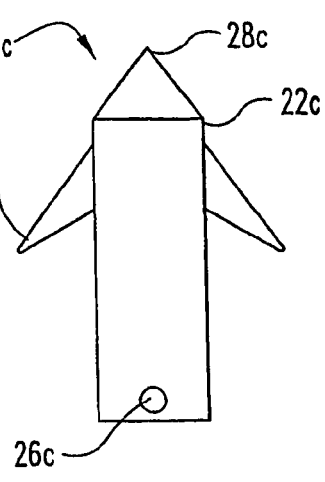
Fig. 3a    Fig. 3b    Fig. 3c
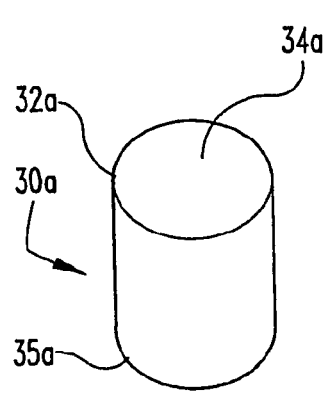
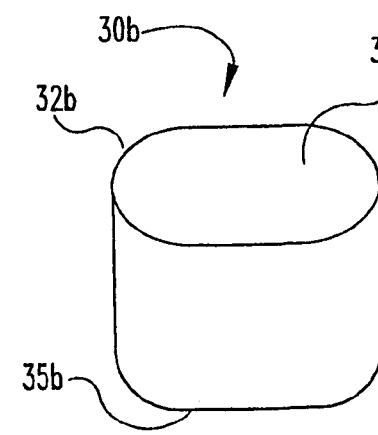
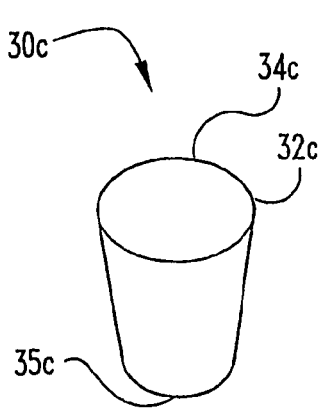
Fig. 4a    Fig. 4b    Fig. 4c
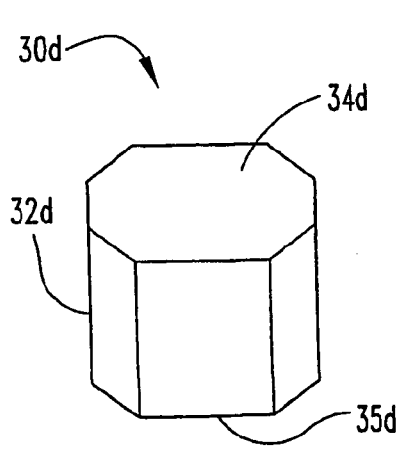
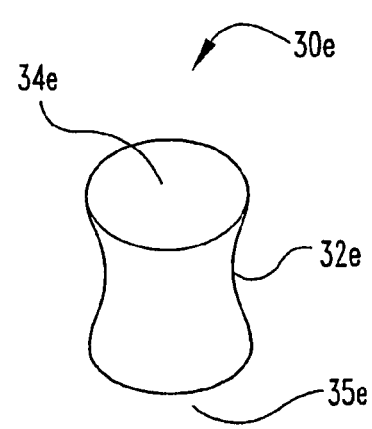
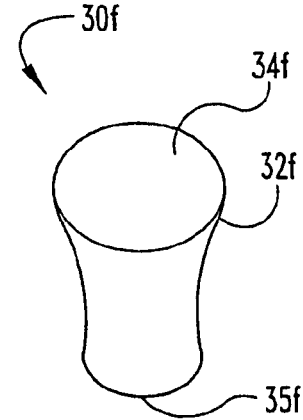
Fig 4d    Fig 4e    Fig 4f

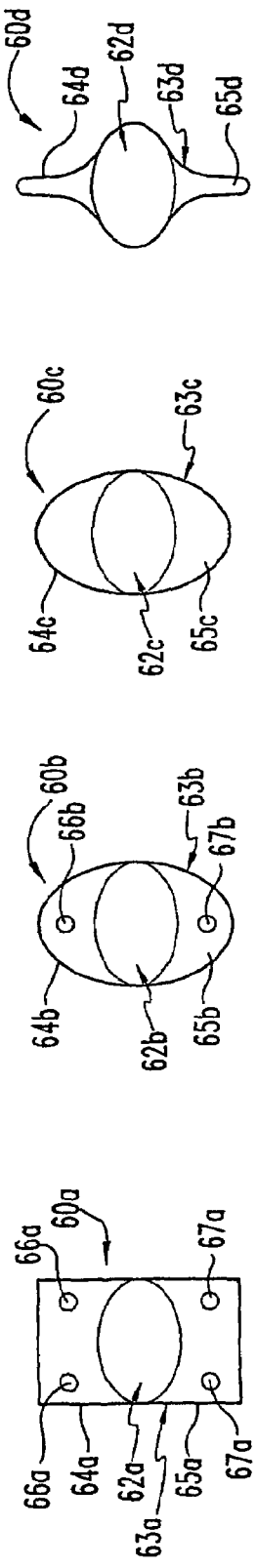
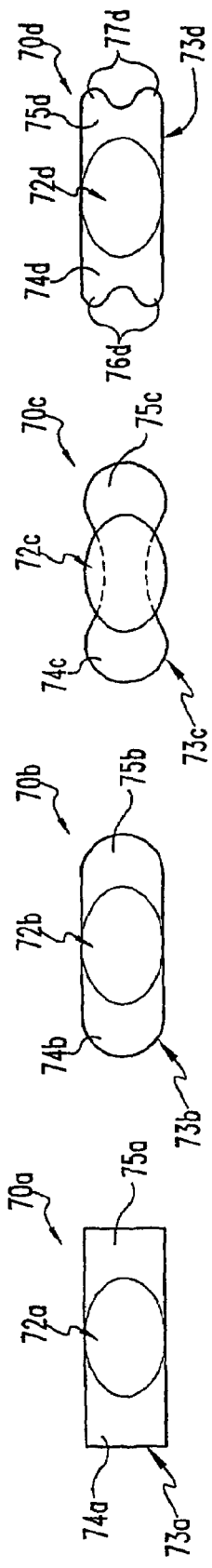
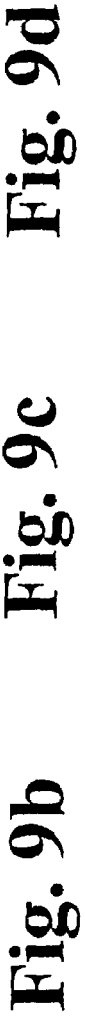
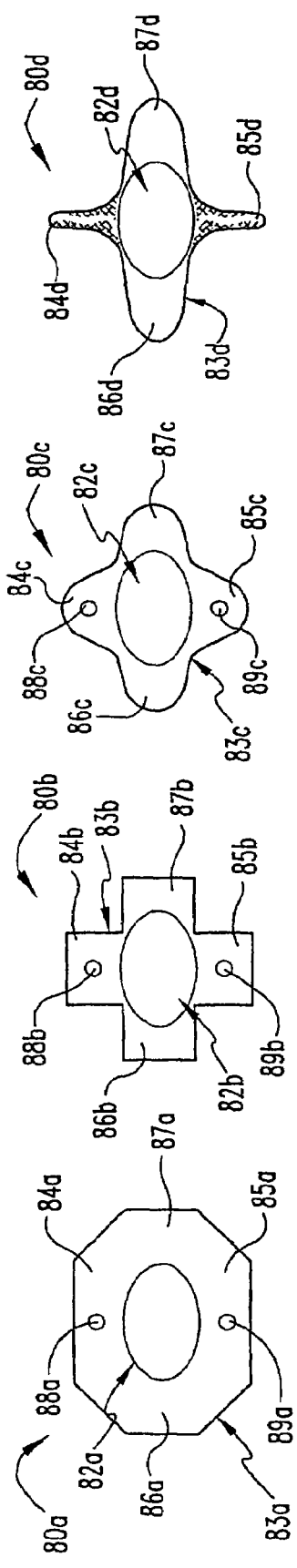

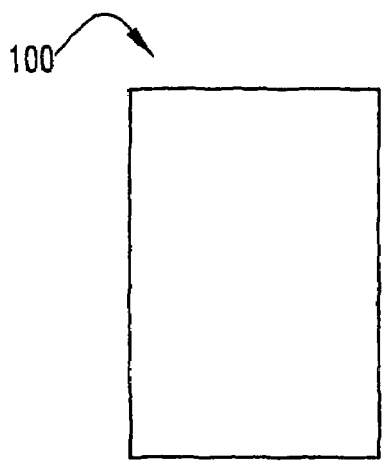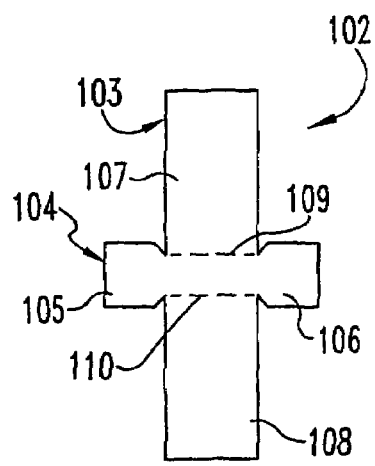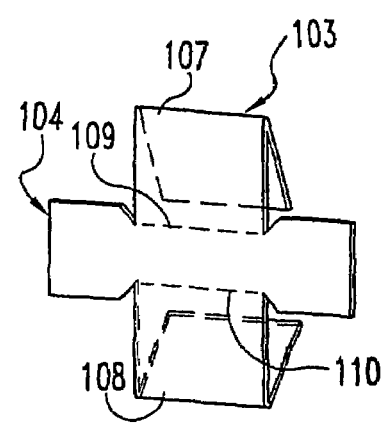
Fig. 12a  Fig. 12b  Fig. 12c
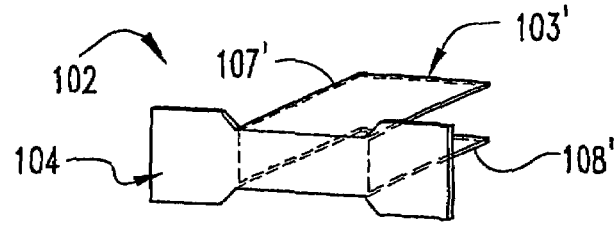
Fig. 12d
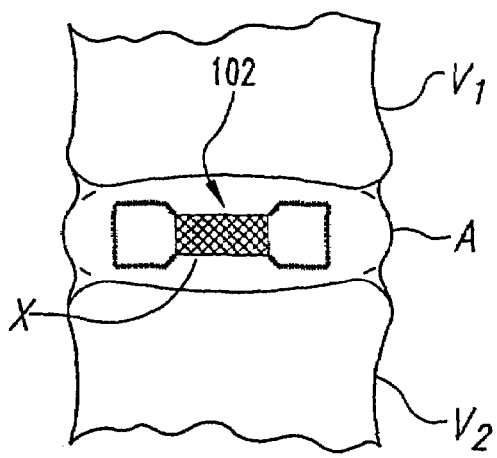
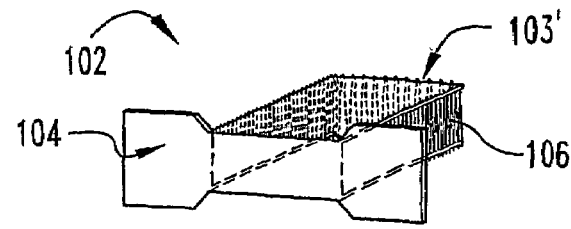
Fig 12f  Fig. 12e

ANNULUS REPAIR SYSTEMS AND METHODS

CROSS-REFERENCE TO RELATED APPLICATION

This application claims the benefit of the filing date of U.S. Provisional Application No. 60/243,941 filed on Oct. 27, 2000.

BACKGROUND OF THE INVENTION

The present invention relates generally to the field of spinal surgery, and more particularly to systems and methods for repairing the annulus fibrosis of a spinal disc.

There are various surgical procedures that create a defect in the annulus fibrosis, such as, for example, an annulotomy, a discectomy, nucleotomy, implantation of artificial disc nucleus or artificial disc prosthesis, or repair of a disc herniation. Repair of annulus defects is normally perceived as time consuming and ineffective. Thus, annulus defects are commonly left unrepaired. This may lead to a higher incidence of disc reherhiation or expulsion of the implant from the disc space.

In those procedures where the annulus is repaired via sutures that attempt to close the defect by pulling the surrounding tissue together, there are difficult challenges encountered. Typically, the annulus defect is a large hole that can be five millimeters or larger in diameter. The size of the hole makes it very difficult to close with conventional suturing techniques since it is difficult to actively engage the sutures in the surrounding annulus tissues. The sutures can also cut or tear through the annulus tissues after the repair has been made.

The prior art includes a surgical device for sealing a biological aperture in situ that is made from a porous expandable material. One disadvantage, however, is that the device could possibly move in the aperture or become dislodged from the aperture.

What is therefore needed is a system and method for spinal surgery which provides a quick and effective repair for defects in the annulus fibrosis which will remain in the defect after placement to seal the opening and/or promote healing. The present invention is directed toward meeting this need, among others.

SUMMARY OF THE INVENTION

The present invention is directed to systems and methods for repairing annulus defects. Embodiments of the system include scaffolds, attachment members, and anchors. The scaffold acts as a plug to substantially fill the annulus defect. The anchors are secured to the vertebral bodies on each side of the disc space. The attachment members secure the scaffold to the anchors.

According to one aspect of the invention, a method for repairing an annulus defect provided. One or more anchors are secured to each of the upper and lower vertebral bodies adjacent the annulus defect site. One or more attachment members are then attached to the anchors. It is contemplated that the attachment members can be attached to the anchors either before or after the anchors are secured to the vertebral bodies. One or more tissue scaffolds are then attached to the attachment members. It is also contemplated that the tissue scaffolds can be attached to the attachment members either before or after the attachment members are attached to the anchors. The scaffold is then inserted into the annulus defect, and the attachment members manipulated to secure the scaffold to the anchors.

In one form of the invention, the scaffold is compressible for insertion into the annulus defect. When the scaffold returns to its normal relaxed state, it substantially seals or fills the defect. An attachment member extends through the scaffold and attaches the scaffold anchors engaged to the adjacent vertebrae.

According to another aspect of the invention, an annulus repair system is provided. One embodiment of the annulus repair system includes a scaffold having an attachment portion. In one form, anchors are used to secure the attachment portion to the adjacent vertebral bodies. In another form, sutures secure the attachment portion to the annulus tissue surrounding the defect. In a further form, the attachment portion is secured to the adjacent vertebral bodies and also to the annulus tissue surrounding the defect.

According to a further aspect of the invention, a non-porous material is positionable in an annulus defect and incorporates into the natural tissue ingrowth.

BRIEF DESCRIPTION OF THE DRAWINGS

FIGS. 3(a)-3(c) illustrate various embodiments of anchors usable with the system of FIG. 1.

FIGS. 4(a)-4(f) illustrate various embodiments of a scaffold usable with the system of FIG. 1.

FIGS. 8(a)-8(d) illustrate various embodiments of a tissue scaffold having an attachment portion for anchoring to bony or hard tissues.

FIGS. 9(a)-9(d) illustrate various embodiments of a tissue scaffold having an attachment portion for anchoring to soft tissues.

FIGS. 10(a)-10(d) illustrate various embodiments of a tissue scaffold having an attachment portion for anchoring to both hard and soft tissues.

FIGS. 12(a)-12(f) illustrates various steps of a method forming a tissue scaffold having an attachment portion from a sheet of fabric or non-woven mesh.

DESCRIPTION OF THE ILLUSTRATED EMBODIMENTS

Figure 1:
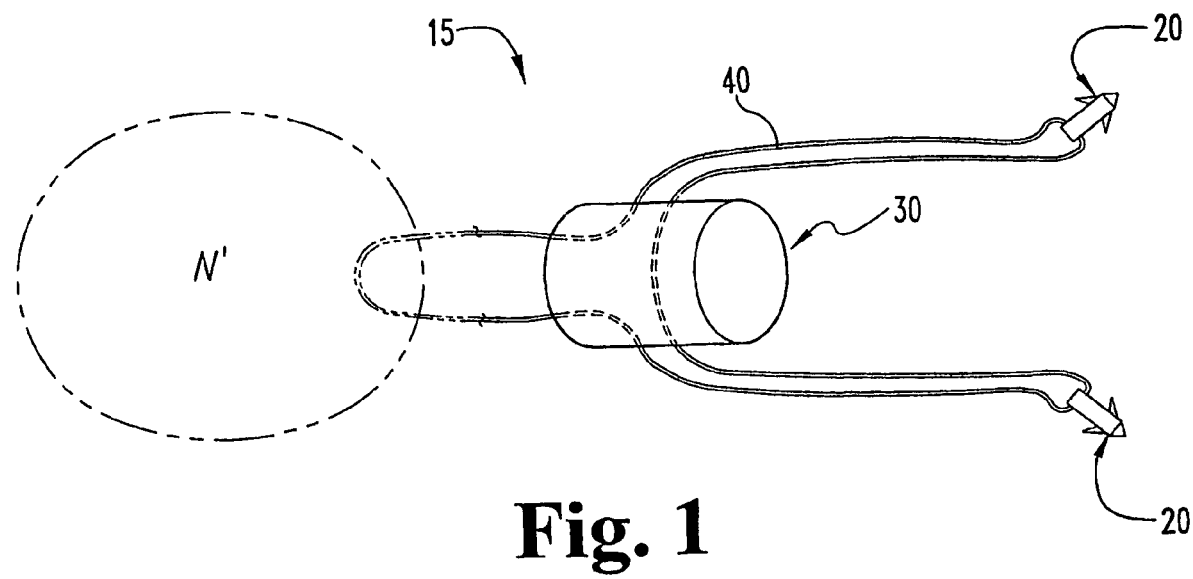
FIG. 1 is directed to one embodiment of an annulus repair system according to one aspect of the present invention.

For the purposes of promoting an understanding of the principles of the invention, reference will now be made to embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The annulus repair system and methods include a tissue scaffold retained by an attachment mechanism within a defect in the annulus fibrosis of a spinal disc. For example, the tissue scaffold substantially fills a defect or void within the annulus fibrosis, such as may be caused by surgery or disc herniation. The tissue scaffold includes a soft tissue ingrowth structure whereby the soft tissue grows through the tissue scaffold and occludes the defect or void. The attachment mechanism is connectable with the tissue scaffold and with anchoring mechanisms. The anchoring mechanisms may be fixedly attached to soft tissue and/or hard tissue or bone adjacent to the defect or void. Thus, the attachment mechanism retains the tissue scaffold in a substantially fixed position within the defect or void relative to adjacent soft or hard tissue.

The scaffold comprises structure that facilitates the formation of natural tissues in the defect space. The scaffold can be resorbable, partially resorbable, or non-resorbable. The tissue scaffold can be any one of or combination of rigid, semi-rigid, compliant, resilient, elastic, compressible, expandable, and/or flexible. The scaffold can be porous, non-porous, or partially porous. For example, the scaffold may be porous, and can be formed from an open or closed cell foam, rolled up woven fabric or non-woven mesh, or braided or woven structures. Additionally, the scaffold may be capable of assuming various shapes that generally conform with the annulus defect. Growth factors or cells can be incorporated into or contained in the scaffold to accelerate the annulus repair process by tissue ingrowth or formation. Growth factors can be transforming growth factor β1, insulin-like growth factor 1, platelet-derived growth factor, fibroblast growth factor, bone morphogenetic protein, and combinations thereof.

In one embodiment the scaffold comprises a non-porous composite structure with at least one resorbable phase and at least one non-resorbable phase. The resorbable and non-resorbable phases are intermingled to form a uniform but heterogeneous material. The resorbable phase is gradually replaced by natural tissues while the non-resorbable phase is incorporated into natural tissue for fixation in order to repair and reinforce the defect. One example of the non-resorbable phase is a three-dimensional woven structure with a mesh size appropriate for cell migration (50-500 microns.) Further examples of non-resorbable materials are provided below. The voids in and/or among the non-resorbable phase are filled with resorbable material. Examples of non-resorbable materials are provided below.

The non-porous tissue scaffold can initially be relatively rigid for insertion. As the resorbable phase absorbs body fluid in vivo, the tissue scaffold becomes more compliant. The non-porous tissue scaffold is gradually incorporated as the resorbable phase is replaced by natural tissue. The tissue scaffold may not be porous as the space originally occupied by the resorbable phase is replaced by natural tissue as the resorbable material is resorbed or removed in vivo. Growth factors or cells can be incorporated into the resorbable phase to further promote tissue ingrowth.

The scaffold can be suturable and tear-resistant, and can be made from any biocompatible material, material of synthetic or natural origin, and material of a resorbable or non-resorbable nature. Suitable examples of scaffold material include autograft, allograft or xenograft; tissue materials including soft tissues, connective tissues, demineralized bone matrix and combinations thereof; resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polypropylene, polyester, polyvinyl alcohol, polyacrylonitrile, polyamide, polytetrafluorethylene, poly-paraphenylene terephthalamide, cellulose, and combinations thereof.

In another form, the scaffold can be of the type discussed in U.S. Pat. No. 6,224,630 which is incorporated herein by reference in its entirety.

The anchors described herein can be made from any biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, and combinations thereof. It is further contemplated that the anchors of the present invention can be any device securable within hard tissue or soft tissue and connectable with a scaffold and/or attachment member.

The attachment members can be any biocompatible material, such as sutures, tethers, cords, planar members, band, wire, cable, mesh, sheet, braid, or any other elongate member capable of retaining the scaffold within an annulus defect and connectable to tissue or to an anchor. Further, attachment member 40 can be resorbable or non-resorbable. Additionally, attachment member and anchors may be combined into a single or integral device.

Referring now to FIG. 1 there is illustrated annulus repair system 15 according to one embodiment of the present invention. The annulus repair system 15 includes a pair of anchors 20, a scaffold 30, and an attachment member 40 movably connectable with scaffold 30 and pair of anchors 20. It should be understood that additional pairs of anchors 20 along with additional attachment members 40 could be provided and connected with scaffold 30.

In another embodiment, one or more attachment members 40 can movably connect one or more artificial disc members N' to scaffold 30 and/or anchors 20. It is contemplated that artificial disc members N' can be an artificial disc nucleus or disc prosthesis, fusion device or some other device that has been inserted into the disc space through defect X in isolation or in combination with one or more other artificial members. Attachment member 40 can extend through the body of artificial disc member N' or through one or more preformed holes.

Figure 2:
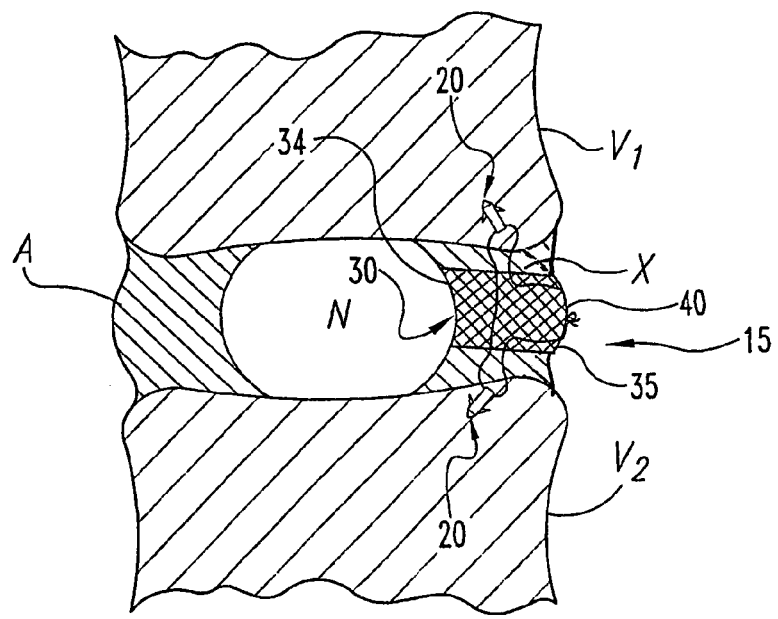
FIG. 2 is the annulus repair system of FIG. 1 positioned in a defect in a spinal disc annulus.

Referring now to FIG. 2, there is shown a sectional view of a spinal column segment including annulus A, nucleus N, upper vertebra V1 and lower vertebra V2. Annulus A includes an annulus defect X. Annulus repair system 15 is shown with scaffold 30 positioned in annulus defect X and secured to the adjacent vertebral bodies V1 and V2. Scaffold 30 includes a first inner end 34 adjacent to or in contact with nucleus N and second outer end 35 generally aligned with the outer surface of annulus A. Anchors 20 are embedded in a respective one of the vertebral bodies V1, V2 through the cortical rim. Attachment member 40 has been pulled through scaffold 30 in order to tightly secure scaffold 30 to the anchors 20.

It is contemplated that defect X in annulus A may have been created in order to perform an annulotomy, discectomy, nucleotomy or some other procedure in the disc space, or the defect X has resulted due to aging, trauma, degenerative condition, or the like. It is further contemplated that nucleus N can be the natural spinal disc nucleus pulposis, or can be an artificial disc nucleus or disc prosthesis, fusion device or some other device that has been inserted into the disc space through defect X. The portion of annulus A surrounding defect X and extending around the nucleus N is substantially intact, or has been repaired using the system and method of the present invention or some other known annulus repair technique.

It is contemplated that scaffold 30 has a length between first end 34 and outer end 35 sufficient to contact nucleus N and extend through defect X to the outer surface of annulus A. The height of scaffold 30 between vertebral bodies V1 and V2, and the width of scaffold 30 along annulus A, is such that scaffold 30 occupies all or substantially all of defect X, thereby effectively sealing defect X.

Referring now to FIGS. 3(a)-3(c), various embodiments of anchor 20 are illustrated. In FIG. 3(a) anchor 20a has shank 22a having a hole 26a formed at one end thereof and an opposite pointed end 28a to facilitate penetration into the vertebral body. A thread form 24a is provided along shank 22a to facilitate rotatable insertion of anchor 20a, and also to resist pullout from the vertebral body once inserted therein. In FIG. 3(b), anchor 20b is provided having a shank 22b with a hole 26b at one end and an opposite pointed end 28b. A number of barbs 24b extend radially and outwardly from shank 22b. Barbs 24b preferably have a downward slope toward hole 26b to resist pull out of anchor 20b from the vertebral body. In FIG. 3(c), anchor 20c includes shank 22c having a hole 26c at one end and an opposite pointed end 28c. A pair of gulls 24c extend outwardly and downwardly from shank 22c towards hole 26c. Gulls 24c are preferably pivotable so that gulls 24c are positioned along shaft 22c during insertion of anchor 20c, and then pivot outwardly to the configuration shown in FIG. 3(c) upon application of a pull-out force so that gulls 24c resist pullout of anchor 20c from the vertebral body.

Referring now to FIGS. 4(a)-4(f), various embodiments of scaffold 30 are provided. In FIG. 4(a) tissue scaffold 30a has a body 32a with a cylindrical shape extending between a first end 34a and an opposite second end 35a. In FIG. 4(b) scaffold 30b has a body 32b with a racetrack or oval shape extending between a first end 34b and an opposite second end 35b. In FIG. 4(c) tissue scaffold 30c has body 32c with a tapered shape that reduces in size as it extends between a first end 34c and an opposite second end 35c. In FIG. 4(d) tissue scaffold 30d has a body 32d with a hexagonal shape extending between a first end 34d and an opposite second end 35d. In FIG. 4(e) tissue scaffold 30e has a body 32e with a circular shape that tapers in size between a first end 34e and an opposite second end 35e to form an overall hourglass shape having a reduced size mid-portion. In FIG. 4(f) tissue scaffold 30f has a body 32f with a circular shape that tapers in size between a first end 34f and an opposite reduced size second end 35f. It is contemplated that first end 34f is positioned adjacent to or in contact with nucleus N, and the larger size of first end 34f resists pushout of body 32f from the annulus defect X. Such anchors could have a funnel shape, mushroom shape, or umbrella shape.

In each of the illustrated embodiments in FIGS. 4(a)-4(f), it is contemplated that scaffold 30 is inserted into the defect in the annulus such that one of the end surfaces 34 or 35 is positioned adjacent the nucleus and the other end surface is positioned along the outer surface of the annulus. It also contemplated that scaffold 30 can be provided with a length that does not extend completely along the length of the defect through the annulus, but rather has an inner end spaced from nucleus N and/or an opposite end that is recessed in the annulus with respect to the outer surface of the annulus.

Figure 5A:
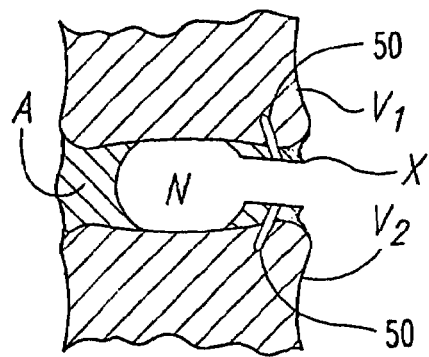
FIGS. 5(a)-5(d) illustrate various steps of one embodiment of a method for repairing an annulus defect using the system of FIG. 1.
Figure 5B:
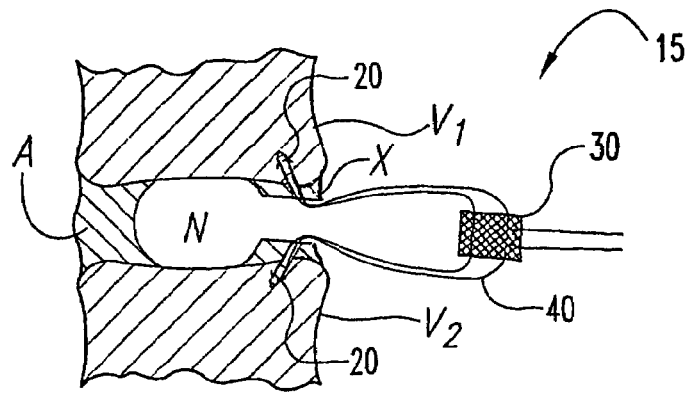
Figure 5C:
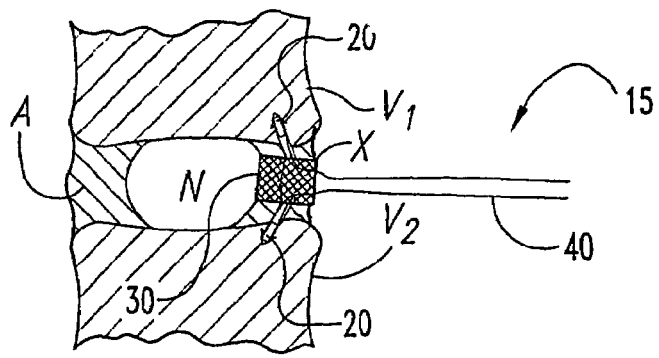
Figure 5D:
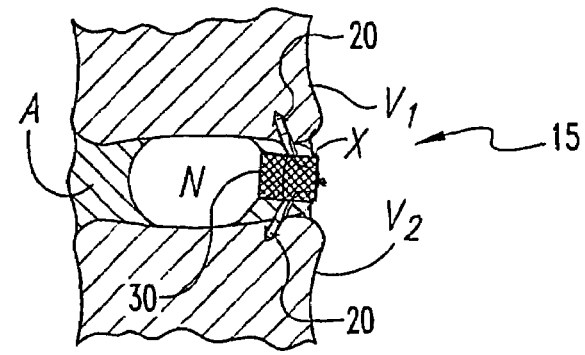

Referring now to FIGS. 5(a)-5(d), various steps of one embodiment of a method using the system of FIG. 1 are shown. In FIG. 5(a) first bore 50 is formed in upper vertebral V1 and a second bore 50 is formed in lower vertebral V2. Anchor bores 50 may be formed at annulus defect X and through the cortical rim of the vertebral end plate of the respective vertebral body. It is also contemplated that bores 50 could be formed at other locations suitable for securing the anchors, such as through the sidewalls of the vertebral bodies. Annulus repair system 15 may then be pre-assembled in a manner as shown in FIG. 1, such that anchors 20 and anchors 30 are movably connected to attachment member 40. In FIG. 5(b) anchors 20 are placed in respective ones of the anchor bores 50. In FIG. 5(c) attachment member 40 has been pulled through scaffold 30, and scaffold 30 positioned into annulus defect X. Scaffold 30 can be compressed or otherwise deformed in order to facilitate insertion into annulus defect X, whereby scaffold 30 returns towards its uncompressed or undeformed configuration to substantially occupy and/or seal defect X. In FIG. 5(d) attachment member 40 is tied or otherwise fixed to secure scaffold 30 in the desired position in defect X. It is also contemplated that anchors 20 can be first embedded into bores 50 without attachment member 40 attached thereto. Attachment member 40 and scaffold 30 are then attached to the embedded anchors 20. It is further contemplated that more than one anchor can be embedded in each vertebrae, and that more than one attachment member can be used to secure scaffold 30 to the one or more embedded anchors.

Referring now to FIGS. 6-12, other forms of the scaffold will be described. The scaffolds of FIGS. 6-12 are similar to scaffold 30 described above, however, the scaffolds of FIGS. 6-12 further include an attachment portion extending from the body portion of the scaffold for direct attachment of the scaffold to the hard and/or soft tissue adjacent the annulus defect. The scaffolds and anchors used with the scaffolds of FIG. 6-12 can be made from the same materials and combinations of materials as scaffolds and anchors discussed above.

Figure 6A:
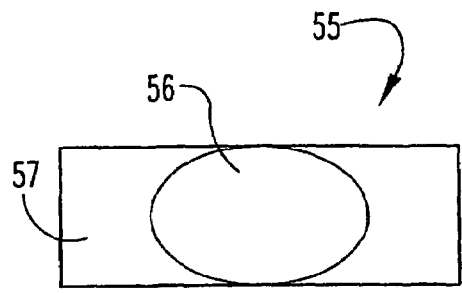
FIGS. 6(a) and 6(b) illustrate a side elevational view and a perspective view, respectively of one embodiment of a tissue scaffold having an attachment portion according to another aspect of the present invention.
Figure 6B:
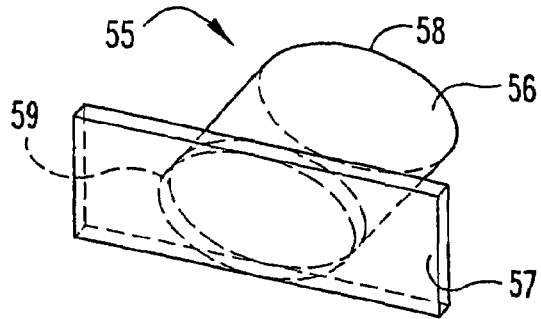

FIGS. 6(a) and 6(b) provide an elevational view and perspective view, respectively, of one embodiment of a tissue scaffold having an attachment portion. Scaffold 55 includes a scaffold body portion 56 insertable in annulus defect X. Body portion 56 has an inner first end 58 positionable towards nucleus N and an opposite outer second end 59 of body portion 56 generally alignable with the outer surface of the annulus tissue surrounding the defect. Scaffold 55 includes an attachment portion 57 connected to or formed with second end 59 that extends outwardly from body portion 56. Attachment portion 57 is preferably flexible and securable to the annulus tissue or the vertebral bodies adjacent to defect X.

Figure 7A:
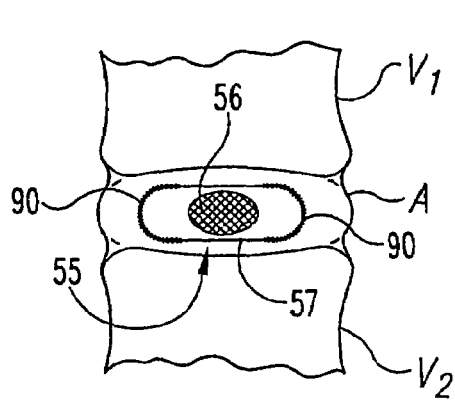
FIGS. 7(a) and 7(b) illustrate the tissue scaffold of FIGS. 6(a) and 6(b) inserted in an annulus defect having an attachment portion secured to the annulus tissue around the defect.
Figure 7B:
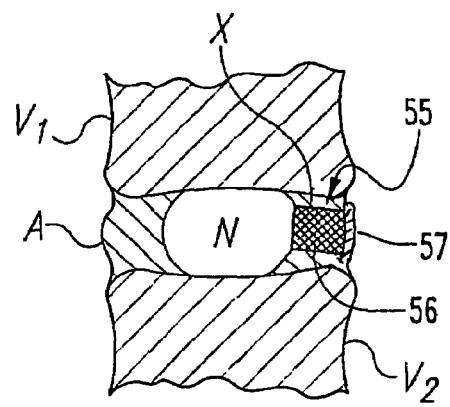

Referring to FIGS. 7(a) and 7(b), scaffold 55 having attachment portion 57 laterally oriented is shown with body portion 56 positioned in annulus defect X. The attachment portion 57 extends along the outer surface of annulus tissue A. Attachment portion 57 is secured to annulus tissue A surrounding annulus defect X via sutures 90 to maintain the positioning of scaffold 55 in the defect.

Referring now to FIGS. 8(a) through 8(d), various embodiments of tissue scaffold 55 having an attachment portion connectable to hard tissue, such as the bony vertebral bodies V1 and V2, is provided. The attachment portions can be secured to the vertebral bodies adjacent annulus defect X via anchors to maintain the positioning of scaffold 55 in the defect.

Figure 11C:
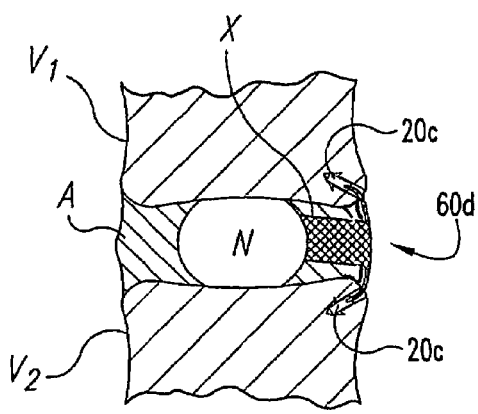
FIGS. 11(a)-11(d) illustrate various tissue scaffolds in an annulus defect having an attachment portion anchored to the adjacent vertebral bodies.
Figure 11D:
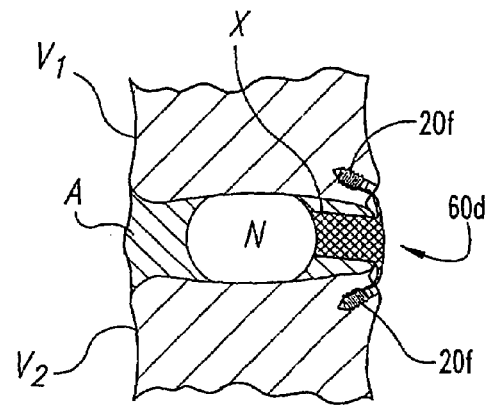
Figure 11A:
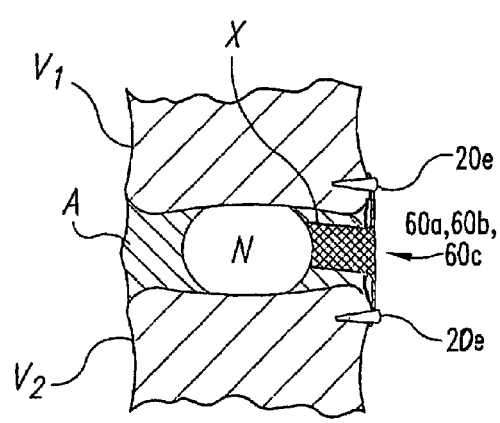
Figure 11B:
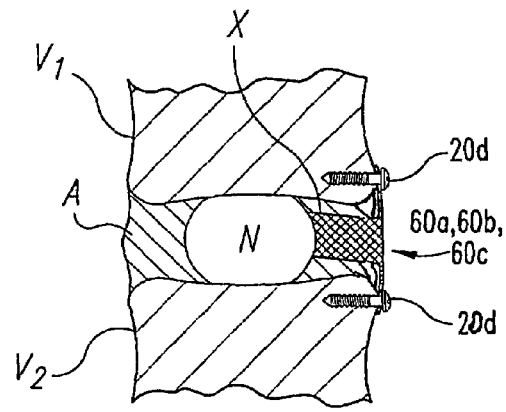

In FIG. 8(a) scaffold 60a includes a scaffold body portion 62a extending between an inner end and an outer end and an attachment portion 63a extending from the outer end of body portion 62a. Attachment portion 63a includes an upper tab 64a having a rectangular shape extending upwardly from body portion 62a and lower tab 65a having a rectangular shape extending downwardly from body portion 62a. Upper tab 64a includes a pair of upper holes 66a, and lower tab 65a includes a pair of lower holes 67a. Anchors, screws, staples pins or other attachment means positionable through holes 66a, 67a can be used to secure the attachment portion to vertebrae V1 and V2. As shown in FIG. 11(a), an anchor in the form of staples 20e are positioned through the tabs to secure scaffold 60a to vertebrae V1, V2. In FIG. 11(b) an anchor in the form of screws 20d are positioned through the holes in the tab to secure scaffold 60a to vertebrae V1, V2.

In FIG. 8(b) scaffold 60b includes a scaffold body portion 62b extending between an inner end and an outer end and an attachment portion 63b extending from the outer end of body portion 62b. Attachment portion 63b includes an upper tab 64b having a semi-circular shape extending upwardly from body 62b and lower tab 65b having a semi-circular shape extending downwardly from body portion 62b. Upper tab 64b includes an upper hole 66b, and lower tab 65b includes lower hole 67b. Anchors, staples, screws, pins or other attachment means positionable through holes 66b, 67b can be used to secure the attachment portion to vertebrae V1, V2. As shown in FIG. 11(a), staples 20e are positioned through the tabs to secure scaffold 60b to vertebrae V1, V2. In FIG. 11(b) screws 20d are positioned through the holes in the tabs to secure scaffold 60b to vertebrae V1, V2.

In FIG. 8(c) scaffold 60c includes a scaffold body portion 62c extending between an inner end and an outer end and an attachment portion 63c extending from the outer end of body portion 62c. Attachment portion 63c includes an upper tab 64c having a semi-circular shape extending upwardly from body 62c and a lower tab 65c having a semi-circular shape extending downwardly from body portion 62c. Suture anchors, screws, pins or staples or other attachment means positionable through the upper and lower tabs 64c, 65c can be used to secure the attachment portion to vertebra V1, V2. As shown in FIG. 11(a), staples 20e are positioned through the tabs to secure scaffold 60c to vertebrae V1, V2. In FIG. 11(b) screws 20d are positioned directly through the tabs to secure scaffold 60c to vertebrae V1, V2.

In FIG. 8(d) scaffold 60d includes a scaffold body portion 62d extending between an inner end and an outer end and an attachment portion 63d extending from the outer end of body portion 62d. Attachment portion 63d includes an upper tab 64d having an elongated, reduced width shape extending upwardly from body 62d and a lower tab 65d having an elongated, reduced width shape extending downwardly from body portion 62d. As shown in FIG. 11(c), these elongated, reduced width tabs can be attached to or engaged by an embedded anchor, such as the gull anchor 20d, with the attachment member partially embedded into vertebrae V1, V2 along with the anchor. In yet another form, the upper and lower tabs can be pushed into bores formed in vertebrae V1, V2, and held in place in the bore by positioning an anchor in the bore alongside the tab, such as threaded interference anchor 20f shown in FIG. 11(d).

In FIGS. 9(a) through 9(d), there are shown various further embodiments of scaffold 55 having an attachment portion connectable to the adjacent annulus tissue surrounding annulus defect X. In FIG. 9(a) scaffold 70a includes a scaffold body portion 72a extending between an inner end and an outer end and an attachment portion 73a extending from the outer end of body portion 72a. Attachment portion 73a includes a first lateral tab 74a having a rectangular shape extending outwardly from body 72a and an opposite second lateral tab 75a having a rectangular shape extending outwardly from body portion 72a. Lateral tabs 74a, 75a can be engaged to the annulus tissue adjacent annulus defect X with sutures, staples, or other suitable attachment means.

In FIG. 9(b) scaffold 70b includes a scaffold body portion 72b extending between an inner end and an outer end and an attachment portion 73b extending from the outer end of body portion 72b. Attachment portion 73b includes a first lateral tab 74b having a semi-circular shape extending outwardly from body 72b and an opposite second lateral tab 75b having a semi-circular shape extending outwardly from body portion 72b. Lateral tabs 74b, 75b can be engaged to the annulus tissue adjacent annulus defect X with sutures, staples, or other suitable attachment means.

In FIG. 9(c) scaffold 70c includes a scaffold body portion 72c extending between an inner end and an outer end and an attachment portion 73c extending from the outer end of body portion 72c. Attachment portion 73c includes a first lateral tab 74c having a semi-circular shape that tapers to a reduced height at body portion 72c, and an opposite second lateral tab 75c having a semi-circular shape extending outwardly from body portion 72c that also tapers to a reduced height at body portion 72c. The tapered lateral tabs 74c, 75c form a figure eight shaped attachment portion 73c. Lateral tabs 74c, 75c can be engaged to the annulus tissue adjacent annulus defect X with sutures, staples, or other suitable attachment means.

In FIG. 9(d) scaffold 70d includes a scaffold body portion 72d extending between an inner end and an outer end and an attachment portion 73d extending from the outer end of body portion 72d. Attachment portion 73d includes a first lateral tab 74d having a pair of laterally extending flanges 76d at the end of the tab opposite body portion 72d. Attachment portion 73d also includes an opposite second lateral tab 75d having a pair of laterally extending flanges 77d at the end of the tab opposite body portion 72d. The lateral flanges on lateral tabs 74d, 75d provide extensions that add perimeter length for suture attachment. Lateral tabs 74d, 75d can be engaged to the annulus tissue adjacent annulus defect X with sutures, staples, or other suitable attachment means.

Referring now to FIGS. 10(a) through 10(d) various embodiments of a scaffold are provided with attachment portions for securement to both hard tissue and soft tissue using the anchors and/or sutures as discussed above. Such attachment portions include any member or combinations of members respectively securable to hard tissue and soft tissue, and in any configuration for retaining a scaffold within an annulus defect.

In FIG. 10(a) scaffold 80a has a body portion 82a and an attachment portion 83a extending from the outer end of body portion 82a. Attachment portion 83a has an upper tab 84a and an opposite lower tab 85a for securement to hard tissue. Upper tab 84a has a hole 88a to receive an anchor, and lower tab 85a has a hole 89a to receive an anchor. Attachment portion 83a also includes opposite laterally extending tabs 86a, 87a for attachment to the soft tissue surrounding the defect. The upper and lower tabs and lateral tabs together form an octagonal shape.

In FIG. 10(b) scaffold 80b has a body portion 82b with attachment portion 83b extending from the outer end of body portion 82b. Attachment portion 83b has an upper tab 84b and an opposite lower tab 85b. The upper and lower tabs 84b, 85b include holes 88b, 89b, respectively, to receive an anchor. Attachment portion 83b also includes first lateral tab 86b and opposite second lateral tab 87b for attachment to the soft tissue surrounding the defect. In this embodiment, the upper and lower tabs and lateral tabs together form a cross shape.

Referring now to FIG. 10(c) scaffold 80c has body portion 82c with attachment portion 83c extending from the outer end of body portion 82c. Attachment portion 83c includes an upper tab 84c having hole 88c to receive an anchor. Attachment portion 83c has a lower tab 85c having a hole 89c to receive an anchor. Attachment portion 83c further includes first lateral tab 86c and opposite second lateral tab 87c for attachment to the soft tissue surrounding the defect. In this embodiment, the upper and lower tabs and the lateral tabs together form an arcuate or curvilinear cross-type shape.

Referring now to FIG. 10(d) scaffold 80d has a body portion 82d with an attachment portion 83d extending from the outer end of body portion 82d. Attachment portion 83d includes upper tab 84d and lower tab 85d. Tabs 84d, 85d have an elongated, reduced width configuration for embedding into the vertebrae V1, V2 as discussed above with respect to the embodiment of FIG. 8(d) and as shown in FIGS. 11(c) and 11(d). Attachment portion 83d also includes first lateral portion 86d and opposite lateral portion 87d for attachment to the soft tissue surrounding the annulus defect.

With respect to the various embodiments of the scaffold having an attachment portion described above, the attachment portion can be joined or fixed to the body portion of the scaffold using various techniques. These techniques include, for example, sewing the attachment portion to the scaffold, thermal welding or bonding, adhesive bonding, three dimensional weaving or braiding, screws, staples, pins, tacks or rivet fixation, or forming the scaffold from existing continuous materials such as folding a sheet of fabric or non woven mesh. Furthermore, the attachment portion can be secured to the body portion of the tissue scaffold either before or after the body portion of the scaffold is placed into annulus defect X.

Referring now to FIGS. 12(a) through 12(f), a technique for forming a tissue scaffold having an attachment portion from a sheet of folded material is provided. In FIG. 12(a) there is provided a sheet 100 that is a sheet of fabric or non-woven mesh material. In FIG. 12(b) a base unit 102 is cut or stamped from sheet 100. Base unit 102 has attachment portion 104 formed by a first lateral tab 105 and an opposite second lateral tab 106. Base 102 further includes a non-folded body portion 103 that has an upper portion 107 that extends upwardly from attachment portion 104 and a lower portion 108 that extends downwardly from its junction with attachment portion 104. Base unit 102 further includes relief portions adjacent the junctions between non-folded body portion 103 and the attachment portion 104 to facilitate folding.

As shown in FIG. 12(c), the upper and lower portions 107, 108 of body portion 103 have each been folded in half, and then folded along fold line 109, 110, respectively, with respect to attachment portion 104 so as to extend outwardly from attachment portion 104 as shown by the folded body portion 103' in FIG. 12(d). As shown in FIG. 12(e) a body portion for a tissue scaffold can be placed between upper and lower portions 107', 108' of holding portion 103'. Upper and lower portions 107', 108' are then attached to one another by threads to hold the body of the tissue scaffold in holding portion 103'. Scaffold 102 may then be inserted into the annulus defect as shown in FIG. 12(f), and the attachment portion 104 sutured, tethered, stapled, or otherwise secured to the soft or hard tissue adjacent to defect X.

While one technique for forming a tissue scaffold is provided above, it should be understood that the tissue scaffolds of the present invention can be fabricated by any technique as would occur to those skilled in the art to which the invention relates.

While embodiments of the invention have been illustrated and described in detail in the drawings and foregoing description, the same is to be considered as illustrative and not restrictive in character, it being understood that all changes and modifications that come within the spirit of the invention are desired to be protected.

What is claimed is:

1. A spinal repair system for repairing an annulus defect of a spinal disc, comprising:
    a scaffold formed as a plug for filling substantially the entire volume of the defect, said scaffold having an outer end aligning with or extending outward from a surface of the annulus and an inner end;
    first and second anchors, each of said anchors having a first end, a second end and a shank between said ends, said shank being cylindrical, said first end being circular and concentric with said shank, and said second end having a point, and wherein said anchors each have a respective hole adjacent said first end having a diameter less than the diameter of said shank; and
    a flexible attachment member, said member having a portion within said scaffold, said member exiting said scaffold at a first point and extending through said hole of said first anchor and returning to and entering said scaffold at a second point adjacent said first point, said member exiting said scaffold at a third point and extending through said hole of said second anchor and returning to and entering said scaffold as a fourth point adjacent said third point.

2. The system of 1, wherein said member is a suture.

3. The system of 1, wherein said member exits said scaffold at fifth and sixth points outside the annulus in two free ends, and said free ends we tied together.

4. The system of 1, wherein the respective shanks of said anchors are non-threaded and include barbs.

5. The system of 1, wherein said annulus defect is adjacent a spinal disc nucleus, and said scaffold inner side is adjacent the nucleus.

6. The system of 1, wherein said annulus defect is adjacent a spinal disc nucleus, and said scaffold inner side is adapted to contact the nucleus.

7. The system of 1, wherein said scaffold is composed of a uniform composite with at least one resorbable phase and at least one non-resorbable phase.

8. The system of 1, wherein said scaffold is adapted to conform to the inner volume of the defect.

9. The system of 1, wherein said scaffold, said anchors and said member are pre-assembled, prior to use in a surgery.

10. The system of 1, wherein said member travels in a continuous manner from said scaffold to and through said hole of said first anchor then through said scaffold and to and through said hole of said second anchor then into said scaffold.

11. The system of 1, further comprising an artificial disc member connected to said attachment member so that said artificial disc member is movable with respect to said attachment member.

12. The system of claim 1, wherein at least one of said anchors are adapted for implantation in bone so that all of said at least one anchor is below the surface of said bone.

13. A method of repairing a defect in an annulus of a spinal disc, comprising:
    providing the system according to claim 1;

placing the first anchor into a first vertebra adjacent the annulus and the second anchor into a second vertebra adjacent the annulus;

positioning the scaffold in the defect; and securing the free ends of the attachment member.

14. The method of claim 13, further comprising forming a first hole in the first vertebra and a second hole in the second vertebra, wherein the placing includes inserting the first anchor into the first hole and the second anchor into the second hole.

15. The method of claim 13, wherein the positioning includes pulling the attachment member through the scaffold.

16. The method of claim 15, wherein the pulling does not pull portions of annulus tissue toward each other.

17. The method of claim 13, wherein the positioning includes compressing the scaffold to facilitate the positioning.

18. The method of claim 13, wherein the securing comprises tying said attachment member.

19. The method of claim 13, wherein the first and second vertebrae have respective endplates, and the placing of the anchors includes placement so that no part of the anchors extends from their respective vertebral endplates.

20. The method of claim 13, further comprising connecting the attachment member to an artificial disc member so that the artificial disc member is movable with respect to the attachment member.

* * * * *